United States Patent [19]

Thompson et al.

[11] 4,381,010
[45] Apr. 26, 1983

[54] HEART PACEMAKER WITH INTEGRATED INJECTION LOGIC ENERGY SAVING CIRCUITRY

[75] Inventors: David L. Thompson, Fridley, Minn.; Donald W. Zobel, Tempe, Ariz.

[73] Assignee: Medtronic, Inc., Minneapolis, Minn.

[21] Appl. No.: 250,640

[22] Filed: Apr. 3, 1981

[51] Int. Cl.³ .............................................. A61N 1/36
[52] U.S. Cl. .............................. 128/419 PG; 307/459
[58] Field of Search ................... 128/419 PG; 307/459

[56] References Cited

FOREIGN PATENT DOCUMENTS 12195 10/1979 European Pat. Off. .
25093 7/1980 European Pat. Off. .

*Primary Examiner*—William E. Kamm
*Attorney, Agent, or Firm*—Merchant, Gould, Smith, Edell, Welter & Schmidt

[57] ABSTRACT

An implantable heart pacemaker having digital injection integrated circuitry includes a bias switch (70) operative to turn on or increase the bias current to the pulse width logic (50) just prior to an output pulse. Increased bias to the pulse width logic permits high speed operation of the logic to accurately terminate the output pulse at the end of the desired pulse duration. At the end of the output pulse, the bias switch is turned off to return the bias current to a low quiescent value, and in some cases is turned completely off, to conserve battery power. The logic gates used in the pulse width logic are arrayed along one or more current injector "bars" or "rails" formed in the integrated circuit, and the bias switch (70) is connected for controlling the current delivered to those current injectors, so that increased bias need only be supplied to the circuits requiring high switching speed.

12 Claims, 2 Drawing Figures

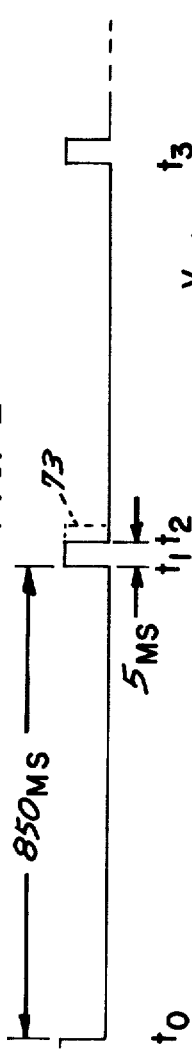
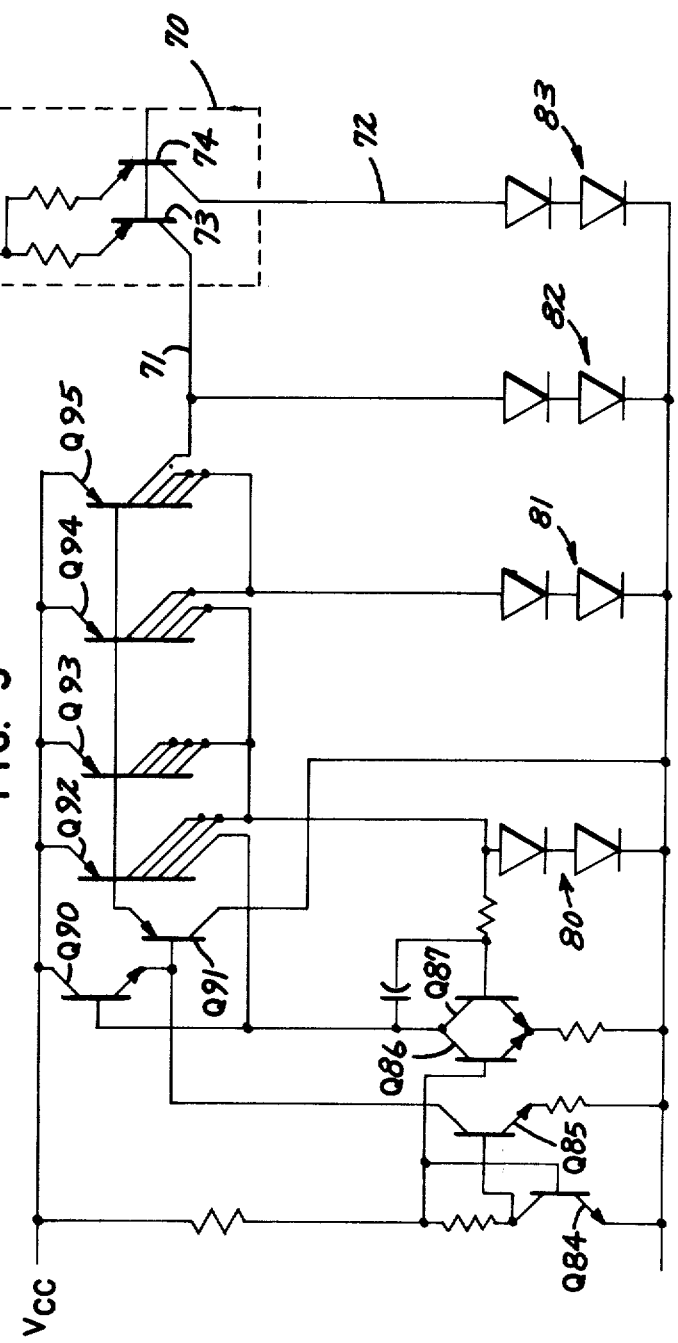
FIG. 2
FIG. 3

HEART PACEMAKER WITH INTEGRATED INJECTION LOGIC ENERGY SAVING CIRCUITRY

TECHNICAL FIELD OF THE INVENTION

The invention pertains to the field of implantable heart pacemakers, and specifically to pacemakers that use digital integrated circuit technology.

BACKGROUND OF THE INVENTION

The introduction in recent years of large scale integrated circuits to the field of implantable pacemakers has contributed to the historical trend in that field toward greater circuit sophistication and flexibility of operation, while at the same time providing smaller physical size and lower power consumption. The additional circuit functions within a given physical size made possible by integrated circuits permit improved pacemaker performance in terms of external programming flexibility and the ability of the pacemaker to respond in different modes of operation as required to meet the needs of the patient in response to an increasing variety of heart conditions or contingencies. The decrease in the physical size of the pacemaker and the potentially lower current drain leading to increased useful life of the implanted device are important advantages of the use of the integrated circuit.

Of the various integrated circuit technologies that have been developed, perhaps the most widely used in heart pacemakers is complementary metal oxide semiconductor (CMOS) technology. Advantages of CMOS technology include very low current drain, reasonably high circuit density leading to a reasonably small sized circuit, and the fact that it is a well proven technology with many years of experience.

Integrated injection logic (I²L) potentially has certain advantages over CMOS technology for an implantable heart pacemaker, but it is also subject to some potential disadvantages. One advantage of I²L is greater circuit density, which potentially leads to an integrated circuit smaller by perhaps a factor of two than the same type of device in CMOS, and of course small size is important in the art of implantable pacemakers. Another potential advantage of I²L is that it is cheaper to develop and build because it involves fewer masking steps and exotic processes like ion implantation, than CMOS. A possible further advantage of I²L, although opinions in the industry are divided on this, is that I²L is not subject to failure due to static buildup, which is sometimes thought to be the case with CMOS.

A particularly attractive advantage of I²L for use in an implantable pacemaker is the compatibility of I²L with analog bipolar technology. The masking and fabrication steps are very similar to bipolar technology, leading to the potential of providing both digital I²L and analog bipolar circuits on the same chip. With present pacemakers using CMOS, most of the digital timing, decoding and control functions are performed on the CMOS chip, while another chip or chips are provided with analog circuits for the pulse output circuit, the sense amplifiers and the RF circuits used in remote programming. With I²L many of these could be incorporated on the same chip as the timing and control logic.

However, I²L is subject to a disadvantage as compared with CMOS in the area of current drain or power consumption. CMOS has inherently low current drain because the quiescent current for the gates is extremely small, whereas I²L gates require a significant bias current. Further, it is known that switching speed in I²L is heavily dependent upon bias current, with switching speed increasing with increasing bias. It is believed to be possible to make an I²L chip to duplicate the functions of present CMOS pacemaker chips at a comparable current drain, by providing a very low bias current to the gates of the I²L chip. However, the resulting slow switching speed of the gates can be a problem, and can cause degraded performance in at least some areas such as output pulse width control. A typical value for output pulse width in a pacemaker might be 0.5 milliseconds, with the exact value being selected by remote programming capability. If the timing and logic circuits responsible for pulse width control are operated at extremely low bias current, the resulting delays in switching time could create an error of perhaps 10 to 15 percent in pulse width control, and this would be considered unacceptable. In the case of circuitry for controlling pacemaker output rate, the relatively longer intervals between output pulses, typically 800 to 900 milliseconds, means that switching speed delays will be proportionately less significant.

SUMMARY OF THE INVENTION

The present invention provides switchable biasing means for implantable heart pacemakers, providing both sufficiently high switching speed and sufficiently low current drain for full and accurate pacemaker performance and long pacemaker battery life. This is accomplished according to the present invention by maintaining bias current low, or off, for circuits while they are not needed, and bringing bias current on, or up to high speed switching levels, just before certain circuits are needed. In the case of output pulse width control logic, bias current for the involved logic gates is maintained at a low level, or in some cases completely off, during the escape interval of the device. Just before an output pulse is delivered, control circuitry increases the bias to the pulse width logic circuits to enable them to perform their timing function with high switching speed. At the end of the output pulse, bias currents are returned to the low, energy saving level. The switchable biasing means of the present invention is especially useful with integrated injection logic integrated circuitry, to bring the benefits of that integrated circuit technology to implantable pacemakers.

BRIEF DESCRIPTION OF THE DRAWING

In the drawing.

FIG. 2 is a waveform illustrating the operation of the pacemaker of FIG. 1; and

FIG. 3 is a simplified schematic showing the bias circuits and control thereof for an I²L integrated circuit of FIG. 1.

DETAILED DESCRIPTION OF THE PREFERRED EMBODIMENT

Figure 1:
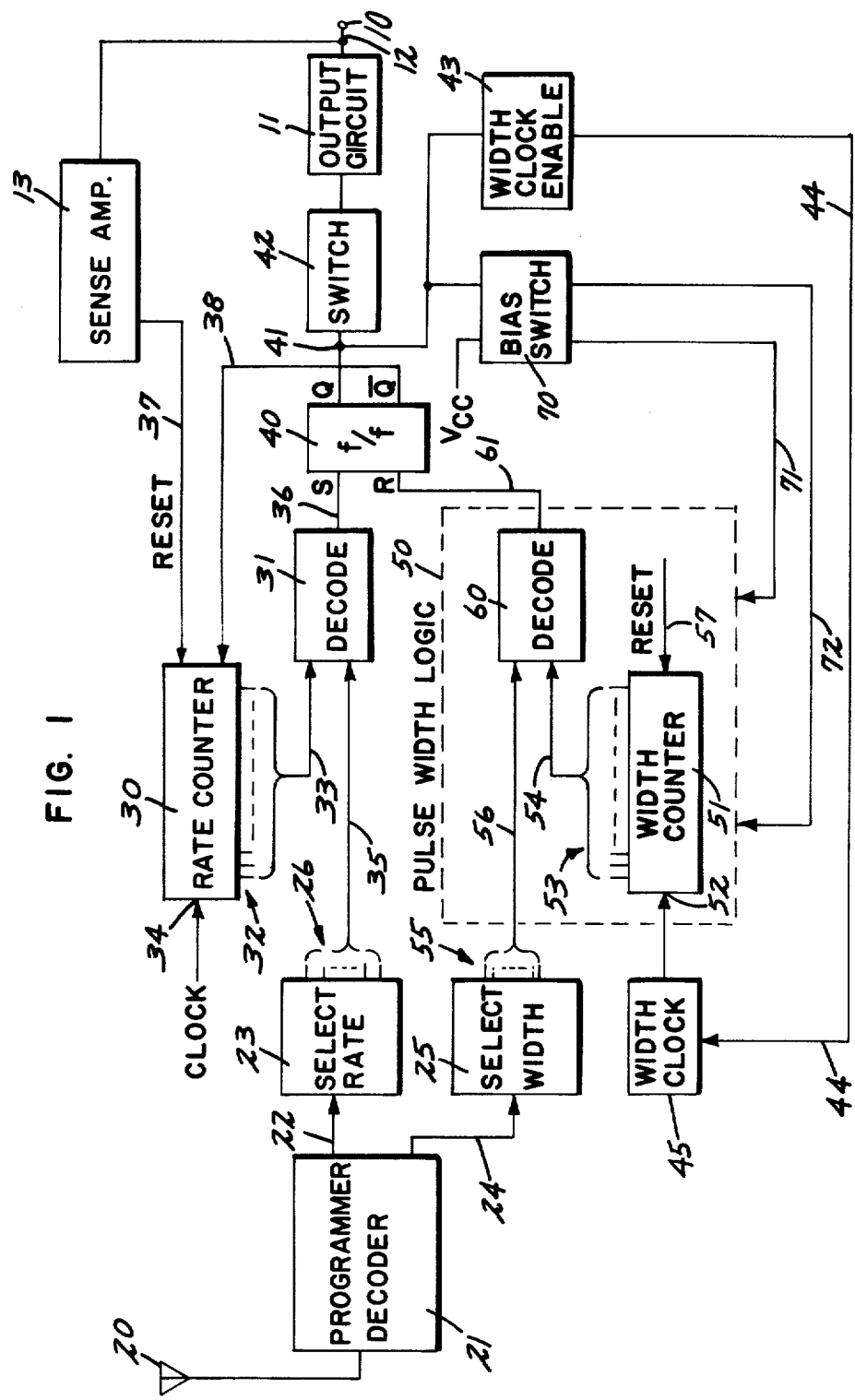
FIG. 1 is an electrical block diagram showing the logic organization of a portion of a pacemaker, incorporating the present invention.

In FIG. 1, a digital implantable pacemaker incorporating the invention is shown in block diagram form. Only certain main components of the pacemaker are shown in order to illustrate the invention, it being understood that additional circuits for additional functions as are generally known in the art, might also be provided.

In FIG. 1 reference number 10 indicates the output terminal of the pacemaker, to which the lead would be connected in use to extend to the heart to deliver stimulation pulses from the pacemaker to the heart. The stimulation pulses are provided by output circuit 11, under control of the pacemaker logic circuits as described hereinafter. Output circuit 11 connects to terminal 10 via conductor 12. A branch of conductor 12 extends to a sensing amplifier 13 which detects spontaneous depolarizations of the heart. The pacemaker shown is a programmable pacemaker so that a number of operating parameters, for example pulse rate and pulse width, can be selected by a remote programming device after the pacemaker is implanted. As is generally known in the art, additional functions can also be selected or controlled by the remote programming, but only pulse rate and width are shown in FIG. 1 in order to illustrate the present invention.

External programming coded signals from the appropriate programming device are transmitted into the body by RF energy and are picked up by antenna 20, which conveys them to programmer-decoder 21. The transmitted signals are decoded and those signals representing the selected pacemaker rate are transmitted over control line 22 to a select rate register 23. In similar manner, the control signals for the selected pulse width are transmitted over control line 24 to the select width register 25. Registers 23 and 25 could be counters or registers, as desired, and the application of data thereto over control lines 22 and 24, respectively, could take the form of parallel bits of data transmitted to the register for storage, or serial bits of data which are then counted and stored in the select rate and select width registers, respectively. In any case, after the programming process has taken place, registers 23 and 25 will contain stored digital data corresponding to the selected pulse repetition rate and pulse width.

Rate control is accomplished by rate counter 30 and rate decoder 31, in conjunction with select rate register 23. Counter 30 consists of a plurality of binary counting stages such as flip-flops connected in series. Outputs from the stages, indicated by reference number 32, are applied via a plurality of data lines, indicated by reference number 33, to decoder network 31. A clock signal is applied to input 34 of the counter. The clock signal may be from a stable oscillator, such as a quartz reference oscillator or other source of timing signals within the pacemaker.

The bits of the rate select data stored in register 23 are applied through outputs, indicated by reference number 26, over a plurality of data lines 35 to additional inputs of decoder 31. Decoder 31 contains a network of logic gates designed to perform the function of digital comparison of the count of rate counter 30 and the rate select data stored in register 23, and to provide at its output, on lead 36, a signal when a predetermined comparison has been reached. Rate counter 30 is reset upon occurrence either of a spontaneous heart contraction, or an output stimulation pulse, by signals applied to its reset inputs from conductor 37, from sense amplifier 13, or from conductor 38 from the output control circuitry.

Following a heart contraction, either spontaneous, or stimulated, counter 30 begins to count clock pulses. At the end of the escape interval corresponding to the selected rate, the count in counter 30 reaches a predetermined correspondence with the rate select data in register 23, and this comparison is detected by decoder 31 which sends a signal on conductor 36 to set flip-flop 40. If a spontaneous heart depolarization occurs prior to the counting out of the selected escape interval, it will be detected by sense amplifier 13, which will reset counter 30 via conductor 37, and the cycle will be restarted.

The setting of flip-flop 40 initiates an output pulse for the pacemaker. The Q output of flip-flop 40 connects through conductor 41 to a switching device 42, which in turn connects to output circuit 11. Output circuit 11 contains the actual switching transistors and capacitors, and may be on the same integrated circuit as the rest of the circuitry in FIG. 1, or, it might be located separately within the pacemaker.

The setting of flip-flop 40 also activates the pulse width logic, which serves to control the duration, or width, of the output pulse, and to terminate the output pulse at the preselected duration. A branch of conductor 41 connects to a width clock enable circuit 43, which connects through control line 44 to width clock circuit 45.

The pulse width logic is indicated by reference number 50, and includes a counter 51 and a decoder 60 which are analogous in function to counter 30 and decoder 31 of the rate control logic. Counter 51 has an input 52 to receive clock pulses from width clock 45, and it has a reset input 57. Counter 51 includes a plurality of outputs for its counter stages indicated by reference number 53. These are connected by a plurality of data lines indicated by reference number 54 to decoder 60.

The selected pulse width is stored as digital signals in register 25, and is available at outputs 55 of register 25. These outputs are conveyed over data line 56 to decoder 60. Decoder 60 is a logic network designed to detect a predetermined correspondence between the width select data on outputs 55, and the state of counter 51 at a given time. It will be appreciated that decoder 60 would typically include a number of logic gates, and also fan-out circuits for the signals from register 25. The output of decoder 60 is conveyed over conductor 61 to the reset input of flip-flop 40.

A branch of conductor 41, from the output of flip-flop 40, connects to bias switch 70, which is also connected to $V_{CC}$, the circuit power source. Switch 70 has outputs 71 and 72 which connect to the bias circuits of the pulse width logic 50, in a manner as described below with reference to FIG. 3.

In operation, after the rate decoding circuitry has set flip-flop 40 to initiate an output pulse via switch 42 and output circuit 11, bias switch 70 increases the bias current to pulse width logic 50, and clock enable circuit 43 starts clock 45. Counter 51 is also reset on power-up. Clock pulses are received and counted in width counter 51 until an output pulse width corresponding to the selected width has been achieved. At that point decoder 60 detects the predetermined comparison of the accumulated count in 51 with the width select data in register 25, and resets flip-flop 40. This terminates the output pulse from output circuitry 11, and also turns off bias switch 70 and clock enable 43. At the same time rate counter 30 is reset via conductor 38, and begins counting the next escape interval.

A typical output from the pacemaker of FIG. 1 is illustrated in FIG. 2. At time $t_0$ a ventricular contraction takes place, either spontaneous or stimulated. Between time $t_0$ and time $t_1$, rate counter 30 is counting out the preselected escape interval, for example 850 milliseconds, corresponding to approximately 70 beats per minute. At $t_1$ flip-flop 40 is set to begin the output pulse. At the same time the pulse width logic is activated and begins counting out the pulse width. At $t_2$ the selected pulse width, 0.5 milliseconds in this example, is reached, and flip-flop 40 is reset and the output pulse is terminated. The escape interval for the next heartbeat cycle begins, resulting eventually in the next output pulse at time $t_3$. It will be appreciated that the escape interval of 850 milliseconds, and the output pulse width of 0.5 milliseconds are not limiting but are only exemplary, as typically a range of values can be selected for each by remote programming as is generally known in the art.

The slow switching speed of I$^2$L gates when operated at low bias current could lead to errors in the delivered pulse width, without the bias switching feature provided by the present invention. For example, if pulse width logic 50 were operated at low, power saving bias levels, pulse propagation delays through the gates could result in delayed turn-off of the pulse width, as indicated by dotted line 73 in FIG. 2. This would have the result of unintentionally increasing the output pulse width, by perhaps 10 to 15 percent. Actually, a similar unintentional lengthening of the escape interval by the pulse rate logic would occur, but the addition of a delay in the order of one-tenth millisecond to the 800 plus millisecond escape interval would not be significant. In the case of pulse width, the error could be significant. Also, the error due to switching delays may not be a constant factor that could be easily compensated for, since it may be a function of the selected rate and the individual gates involved for each selected width.

The physical architecture of an I$^2$L integrated circuit consists of arrays of basic gates or logic cells, each consisting of vertical multiple-collector inverse mode npn transistors, driven by lateral pnp transistor current sources. A series of elongate p-type injector "bars" or "rails" which are formed in the chip extend across it, and the individual logic gates or cells are arrayed alongside the injector bars, so that a single p-type injector bar formed within the integrated circuit chip serves as a portion of the current source for a large number of logic cells positioned alongside it. For example, see "I$^2$L from the linear viewpoint", *Electronics Magazine*, Apr. 13, 1978, page 102–103. Interconnections of the various logic gates to perform the intended logic function are formed by additional layers on the chip as is generally known in the art.

The biasing technique for the I$^2$L pacemaker of FIG. 1 is indicated in FIG. 3. Reference numbers 80, 81, 82, and 83 indicate respectively four p-type injector bars or rails in the chip. Specifically, each injector rail, which is modeled in FIG. 3 as a pair of diodes, forms the current source for the plurality of logic cells arrayed alongside it. The circuit of FIG. 3 has four such rails 80–83 to serve the total number of logic cells of the chip, but it will be appreciated that a greater or lesser number can be provided.

Multiple-collector transistors Q92, Q93, Q94, and Q95 provide the current to injectors 80, 81, and partially to injector 82 through the connections shown. Transistors Q92–Q95 are controlled by transistors Q90 and Q91. Transistors Q84–Q87 and associated components provide a reference and feedback for stabilizing Q91, and for controlling the current through transistors Q92–Q95.

In laying out the integrated circuit, the logic gates used with the pulse width logic 50 of FIG. 1 are grouped to operate from injectors 82 and 83, while the remaining logic circuits of the pacemaker not requiring high switching speed are grouped to operate from injectors 80 and 81. The bias current for injectors 80 and 81 is set at a low value consistent with low power consumption and long battery life, through suitable design of the biasing network components and supply transistors Q92–Q95.

In the case of the pulse width logic circuits, some circuits, for example the decode logic 60, are operated from injector 82 and are maintained at a low bias current through the path from Q95 until just before the occurrence of an output pulse. At that time bias switch circuit 70 serves to increase the bias through injector 82, via path 71. Other circuitry within pulse width logic 50, for example counter 51, is maintained in an off condition during the escape interval between output pulses, and all bias for the logic circuits operating from injector 83 comes from bias switch 70 via path 72 during the output pulse.

A portion of bias switch 70 is also shown in FIG. 3. When flip-flop 40 of FIG. 1 is set by the rate circuitry to initiate an output pulse, transistors 73 and 74 are turned on to supply bias current from $V_{CC}$ through current limiting resistors to injectors 82 and 83. The switching of switch 70 to step up or establish bias current occurs just prior to the start of the output pulse due to inherent slight propagation delays of the latter through switch 42 to the output circuit 11. In the case of injector 82, the switching of circuit 70 increases the quiescent current already provided by Q95, to a level to assure the desired high speed switching characteristics of the decode logic during the pulse interval. In the case of injector 83, transistor 74 provides sufficient bias current to activate the circuits for the desired high speed operation. A reset 57 is also provided upon power up to counter 51 to clear the counter to start the pulse width count sequence previously described.

It will be appreciated from the foregoing description that the biasing and bias switching techniques provided by this invention allow low, power-saving quiescent currents during the escape interval of the pacemaker, which is to say during the vast majority of time, while providing a step up in bias current to levels that permit high speed operation of the pulse width logic, just prior to and during the output pulse, with a return to low quiescent current until the next output pulse. When used in integrated injection logic circuitry the present invention permits the I$^2$L advantages of small size and bipolar circuitry compatibility to be realized in a digital heart pacemaker, while preserving long battery life.

What is claimed:

1. In a digitally controlled implantable heart pacemaker, a plurality of logic circuits interconnected to perform pacemaker control functions, first bias means for supplying bias current to a first group of said logic circuits, a second bias means for providing a switchable bias current to a second group of said logic circuits, and control means for controlling said second bias means and operative to increase bias current to said second group of logic circuits at selected intervals to increase the switching speed thereof during said selected intervals.

2. Apparatus according to claim 1 wherein said control means is operative to increase said bias current at selected intervals which include the time of the stimulating output pulse of the pacemaker.

3. Apparatus according to claim 1 wherein said second group of logic circuits comprises pulse width control logic for the pacemaker.

4. Apparatus according to claim 1 wherein said second bias means switches some of said logic circuits of said second group from a bias off to a bias on condition during said selected intervals, and switches other logic circuits of said second logic group from a low bias to a high bias current condition during said selected intervals.

5. An integrated injection logic circuit for an implantable heart pacemaker comprising a plurality of logic cells or gates interconnected to perform pacemaker control functions including rate control logic for initiating a pacemaker output pulse at the end of a predetermined escape interval from a previous heart depolarization and pulse width control logic for terminating the pacemaker output pulse at a predetermined pulse duration, bias circuits for supplying bias current to the logic gates, a separate bias circuit for logic gates of the pulse width control logic, and bias switching circuit means connected for increasing bias current to said separate bias circuit upon initiation of a pacemaker output pulse and for reducing bias to said separate bias circuit during escape intervals between pacemaker output pulses.

6. An integrated injection logic circuit for an implantable heart pacemaker according to claim 5 wherein said bias switching circuit means is operative to increase bias current to said separate bias circuit just prior to the initiation of a pacemaker output pulse.

7. An integrated injection logic circuit for an implantable heart pacemaker according to claim 5 wherein said bias switching circuit means is operative to switch said bias current between a low value during the escape intervals between pacemaker output pulses and a higher value during the pacemaker output pulse.

8. An integrated injection logic circuit for an implantable heart pacemaker according to claim 5 wherein said bias switching circuit means is operative to turn said separate bias current off during escape intervals between pacemaker output pulses and to turn it on during pacemaker output pulses.

9. An integrated injection logic circuit for an implantable heart pacemaker according to claim 5 including a pair of separate bias circuits for supplying bias current to separate groups of logic gates, respectively, within the pulse width control logic, and wherein said bias switching circuit means is connected for increasing the bias current to one of said separate bias circuits from a low bias to a high bias condition during a pacemaker output pulse and for increasing the bias current in the other separate bias circuit from an off condition to an on condition during a pacemaker output pulse.

10. An implantable heart pacemaker having low power consumption, comprising:
    terminal means for connection to a patient's heart;
    pulse generating means connected to said terminal means and operative when activated to deliver output stimulating pulses thereto;
    rate control means operative to periodically activate said pulse generating means to deliver output stimulation pulses;
    pulse width control circuitry operative when said pulse generating means is activated to time a preselected output pulse width interval and to thereafter deactivate said pulse generating means to terminate the output stimulating pulse after the preselected duration; and
    bias control means operatively connected for providing bias current to the individual switching circuits of said pulse width control circuitry at a magnitude to permit high speed switching thereof when said pulse width control circuitry is timing said preselected output pulse width interval, and thereafter to reduce the bias current thereto to reduce power consumption.

11. A pacemaker according to claim 10 wherein said bias control means turns off the bias current to some circuits of said pulse width control circuitry after the output pulse width interval.

12. A pacemaker according to claim 10 wherein said bias control means reduces said bias current to a low magnitude during intervals between output stimulating pulses.

* * * * *